(12) United States Patent
Tearney et al.

(10) Patent No.: US 6,706,004 B2
(45) Date of Patent: Mar. 16, 2004

(54) BALLOON CATHETER

(75) Inventors: Guillermo J. Tearney, Cambridge, MA (US); Brett E. Bouma, Quincy, MA (US); S. Eric Ryan, Hopkinton, MA (US); Simon Furnish, Louisville, KY (US); Jing Tang, Allston, MA (US); Andres Zuluaga, Boston, MA (US)

(73) Assignee: Infraredx, Inc., Cambridge, MA (US)

( * ) Notice: Subject to any disclaimer, the term of this patent is extended or adjusted under 35 U.S.C. 154(b) by 357 days.

(21) Appl. No.: 09/871,771

(22) Filed: May 31, 2001

(65) Prior Publication Data

US 2002/0183620 A1 Dec. 5, 2002

(51) Int. Cl.[7] .............................................. A61B 5/103
(52) U.S. Cl. .................... 600/587; 600/473; 604/99.01; 606/194
(58) Field of Search ..................... 604/99.01; 600/473, 600/587, 476, 478, 322, 341, 342, 309, 115–117, 504, 505; 606/2, 3, 7, 10, 13–16, 191–194; 607/88, 92

(56) References Cited

U.S. PATENT DOCUMENTS

| | | | |
|---|---|---|---|
| 3,057,345 A | 10/1962 | Ferris et al. ................... 128/8 |
| 4,217,045 A | 8/1980 | Ziskind ........................ 354/62 |
| 4,292,961 A | 10/1981 | Kawashima ................... 128/6 |
| 4,924,863 A | 5/1990 | Sterzer ........................ 606/27 |
| 5,007,919 A | 4/1991 | Silva et al. |
| 5,125,925 A * | 6/1992 | Lundahl ...................... 606/15 |
| 5,347,987 A | 9/1994 | Feldstein et al. ............ 600/109 |
| 5,381,786 A * | 1/1995 | Spears ....................... 600/117 |
| 5,609,591 A | 3/1997 | Daikuzono ................... 606/15 |
| 5,895,397 A | 4/1999 | Jang et al. ................... 606/159 |
| 5,916,210 A | 6/1999 | Winston ........................ 606/7 |
| 5,919,145 A | 7/1999 | Sahatjian ..................... 600/572 |
| 6,022,319 A | 2/2000 | Willard et al. .............. 600/470 |
| 6,029,076 A | 2/2000 | Fiddian-Greene et al. .. 600/353 |
| 6,106,515 A | 8/2000 | Winston et al. ............... 606/15 |
| 6,491,618 B1 * | 12/2002 | Ganz ............................. 600/3 |
| 6,522,913 B2 * | 2/2003 | Swanson et al. ............ 600/478 |
| 6,579,301 B1 | 6/2003 | Bales et al. |
| 2001/0003800 A1 * | 6/2001 | Crowley ...................... 607/88 |
| 2001/0020126 A1 * | 9/2001 | Swanson et al. ............ 600/407 |
| 2001/0041860 A1 | 11/2001 | Barbut |
| 2002/0052621 A1 * | 5/2002 | Fried et al. .................. 606/192 |
| 2002/0120182 A1 * | 8/2002 | Muessig et al. ............. 600/178 |
| 2003/0135122 A1 * | 7/2003 | Bambot et al. ............. 600/476 |

* cited by examiner

*Primary Examiner*—Brian L. Casler
*Assistant Examiner*—Jeremy Thissell
(74) *Attorney, Agent, or Firm*—Fish & Richardson, P.C.

(57) ABSTRACT

An apparatus includes a feedback loop for controlling an extent of a gap between a wall of a balloon mounted on a catheter and a wall of a lumen into which the catheter is inserted. The apparatus includes a radiation detector mounted within the balloon for generating a feedback signal having information indicative of whether the extent of the gap is greater than or less than a desired value. The feedback loop receives the feedback signal and controls a size of the balloon to cause the extent of the gap to approach the desired value.

30 Claims, 5 Drawing Sheets

BALLOON CATHETER

TECHNICAL FIELD

This invention relates to catheters, and more particularly to balloon catheters.

BACKGROUND

Certain types of plaques in a patient's vasculature are likely to rupture. These plaques, once ruptured, are extremely dangerous and can swiftly cause the patient's death. It is therefore desirable to detect the existence of such high-risk plaques so that they can be disposed of before they rupture.

High-risk plaques are believed to be characterized by large lipid pools hidden behind vascular walls. Because these lipid pools are covered by vascular walls, they cannot be seen by visible light. However, infrared light can penetrate short distances into the vascular wall and can therefore be used to detect such plaques, as well as other intravascular pathology.

A difficulty associated with intravascular use of infrared radiation is that blood absorbs and scatters such radiation. This results in a reduction in the signal-to-noise ratio. As a result, it is desirable to minimize the extent to which infrared radiation propagates through the blood.

One approach to removing blood from a measurement site is to purge or flush the site with saline. This technique provides a short window of opportunity during which a measurement can be taken through the transparent saline. However, once the saline disperses, blood flows back into the measurement site and obscures the vascular wall.

Another approach to removing blood from a measurement site is to displace it with an inflated balloon catheter. However, if the balloon is not sufficiently inflated, considerable blood remains between the balloon and the vascular wall. If the balloon is so inflated that it makes contact with the vascular wall, blood flow is obstructed. This can lead to ischemia at points downstream from the balloon. In addition, the pressure of the balloon on the vascular wall can trigger a rupture of the plaque.

SUMMARY

The invention is based on the discovery that if the inflation level, and hence diameter, of a catheter balloon is carefully controlled in real time, the balloon can displace a maximal amount of blood without touching the inner wall of the blood vessel. This reduces scattering and absorption by the blood while avoiding irritation and injury to the inner walls of the blood vessel.

The present invention features catheters for inspecting intravascular structure with infrared radiation. The catheters include balloons that can be inflated to displace blood from the field of view. The extent to which the balloon is inflated is controlled by a feedback loop in which the measured extent of a gap between the outer wall of the balloon and the inner wall of the blood vessel is compared with a desired extent of that gap. The difference between the measured extent and the desired extent provides a basis for either inflating or deflating the balloon.

Another aspect of the invention features a plurality of individually controllable balloons circumferentially disposed around a catheter. A corresponding plurality of measurements provides an estimate of the gap between each of the circumferentially disposed balloons and an arcuate segment of the vascular wall directly opposed from that balloon. By individually controlling each of the balloons, the catheter can be centered within the blood vessel.

In one embodiment, the invention provides an apparatus for controlling an extent of a gap between a wall of a balloon mounted on a catheter and a wall of a lumen into which the catheter is inserted. The apparatus includes a radiation detector or optical fiber mounted within the balloon for generating a feedback signal having information indicative of whether the extent of the gap is greater than or less than a desired value, and a feedback loop for receiving the feedback signal and controlling a size of the balloon to cause the extent of the gap to approach the desired value.

In another embodiment, the invention provides an apparatus having a catheter for insertion into a lumen and a balloon disposed on the catheter. The balloon defines a gap between a wall of the lumen and a wall of the balloon. A radiation source is disposed within the balloon for transmitting radiation through the balloon wall and into coupling fluid present in the gap. The apparatus also includes a feedback loop having a radiation detector or optical fiber disposed within the balloon to receive radiation from the coupling fluid through the balloon wall, and a processor in communication with the radiation detector for determining, on the basis of a signal provided by the radiation detector, a measured extent of the gap. A controller in communication with the processor controls the inflation of the balloon to achieve a desired extent of the gap in response to the measured extent of the gap.

The radiation source can be an infrared emitter and the radiation detector can be an infrared detector. However, the principles of the invention are applicable to emitters and detectors adapted for operation at other frequencies of electromagnetic radiation. In addition, the radiation emitter and detector need not operate at the same frequencies.

The processor can be configured to determine the extent of the gap on the basis of absorption of radiation transmitted by the radiation source, the extent of the absorption being indicative of the extent of the gap. Alternatively, the processor can be configured to determine the extent of the gap on the basis of velocity of coupling fluid in the gap, the velocity of the coupling fluid being indicative of the extent of the gap. In one aspect of the invention, a calibration database in communication with the processor provides information to enable the processor to correct for variations due to wave propagation effects that vary among individuals.

The controller can be configured to control inflation of the balloon by changing a quantity of control fluid in the balloon. The quantity of control fluid can be changed by incremental amounts until the difference between the measured extent of the gap and the desired extent of the gap is within a pre-selected range. Alternatively, the quantity can be changed by an amount that depends on the difference between the measured extent of the gap and the desired extent of the gap.

In another embodiment of the invention, a plurality of balloons is circumferentially disposed around the distal end of the catheter. Each balloon has a size that can be controlled by the controller independently of the other balloons. An embodiment having a plurality of balloons is useful to center the catheter within a lumen or to maintain a spatially constant gap between the wall of each balloon and the wall of the lumen when the cross-section of the lumen is not circular.

The method also includes methods for controlling an extent of a gap between a wall of a balloon mounted on a catheter and a wall of a lumen into which the catheter is inserted.

In one practice, the method includes obtaining a feedback signal having information indicative of whether the extent of the gap is greater than or less than a desired value. In response to the feedback signal, the size of the balloon is controlled to cause the extent of the gap to approach the desired value.

In another practice, the invention includes a method for controlling an extent of a gap between a wall of a balloon catheter and a wall of a lumen, the gap being filled with a coupling fluid. The method includes transmitting first radiation through the coupling fluid and receiving second radiation. The second radiation contains information indicative of propagation effects encountered by the first radiation. On the basis of the second radiation, a measured extent of the gap is determined. The balloon is then inflated to minimize a difference between the measured extent of the gap and a desired extent of the gap.

In one aspect of the invention, the transmitted radiation is infrared radiation. However, the method can include transmitting radiation having any frequency. Similarly, the detected, or received radiation can be infrared radiation. However, the method can include receiving radiation at any frequency. In addition, the frequency of received radiation need not be the same as the frequency of transmitted radiation.

To remove the effect of propagation differences that vary between patients, it is useful to obtain measurements at more than one wavelength. In one aspect, the invention provides for transmitting radiation at a first wavelength at which propagation effects in the coupling fluid are dominated by a first constituent of the coupling fluid. In another aspect, the invention provides for transmitting radiation at a second wavelength at which propagation effects in the coupling fluid are dominated by a second constituent of the coupling fluid. More generally, the invention provides for selecting a plurality of wavelengths and transmitting radiation at each of the plurality of wavelengths.

The received radiation can be attenuated radiation, the extent of the attenuation being indicative of the extent of the gap. Alternatively, the received radiation can be frequency shifted from the transmitted radiation by an amount indicative of the difference between the first and second wavelengths being indicative of velocity of the coupling fluid, the velocity of the coupling fluid being indicative of the extent of the gap.

Because of physiological differences between patients, it is useful to correct for such differences when determining the measured extent of the gap. This can include removing scattering and absorption effects resulting from propagation of the first radiation through the coupling fluid. Alternatively, this can include removing effects from pulsatile flow of the coupling fluid.

In another aspect of the invention, controlling inflation of the balloon catheter includes delivering control fluid to the catheter balloon when the desired extent of the gap exceeds the measured extent of the gap and withdrawing control fluid from the catheter balloon when the measured extent of the gap exceeds the desired extent of the gap. This can be achieved by changing a quantity of control fluid in the catheter balloon incrementally until the difference between the measured extent of the gap and the desired extent of the gap is within a pre-selected range. Alternatively, the quantity of control fluid can be changed by an amount that depends on the difference between the measured extent of the gap and the desired extent of the gap.

In another practice of the invention, transmitting radiation through the coupling fluid includes defining a plurality of radial directions, each of the radial directions extending radially outward from a longitudinal axis of the catheter, and transmitting a corresponding plurality of radiation beams in each of the radial directions. In one aspect, inflation of each of a plurality of balloons circumferentially disposed around the longitudinal axis of the catheter is individually controlled. The extent to which each balloon is inflated is selected to achieve a pre-selected gap between the balloon and the wall of the lumen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides many advantages, including a high signal-to-noise ratio resulting from a reduction in the extent to which infrared radiation passes through blood. In addition, the invention reduces the risk of injury to the inner wall of the blood vessel that can result from contact with the balloon.

Other features and advantages of the invention will be apparent from the following detailed description, and from the claims.

DESCRIPTION OF DRAWINGS

Like reference symbols in the various drawings indicate like elements.

DETAILED DESCRIPTION

The present invention features catheters that are designed to increase the signal-to-noise ratio of infrared measurements in a blood vessel. The term "infrared" as used herein includes both the far infrared and the near infrared.

The catheters include one or more balloons that displace a coupling fluid, such as blood, from the field of view, thereby enabling infrared radiation to propagate for greater distances without interference from blood. The balloon(s) is/are made of a biocompatible material that is transparent to radiation at the frequencies to be used for measurement, for example in the near infrared. Suitable materials for balloons include polyvinyl chloride and polyethylene. Typical thicknesses of the balloon wall are in the range of 5 to 100 micrometers.

The principles of the invention are not restricted to infrared radiation but are equally applicable to electromagnetic radiation having wavelengths outside the infrared range. In particular, the principles of the invention can be applied to electromagnetic radiation at optical frequencies. Although this detailed description teaches one particular embodiment in which measurements are made in the infrared range, the scope of the invention is not limited to infrared frequencies.

An apparatus incorporating the invention provides a feedback loop for controlling the extent to which the balloon(s) displace(s) blood from the field of view. In the feedback loop, real-time measurements are made of an extent of a gap between the balloon(s) and the wall. The extent of balloon inflation, and thus the gap(s) between the balloon(s) and the inner wall of the blood vessel, is/are adjusted in real time to assure that the balloon(s) avoid(s) blocking the flow of blood by coming into contact with the vessel wall.

Figure 1:
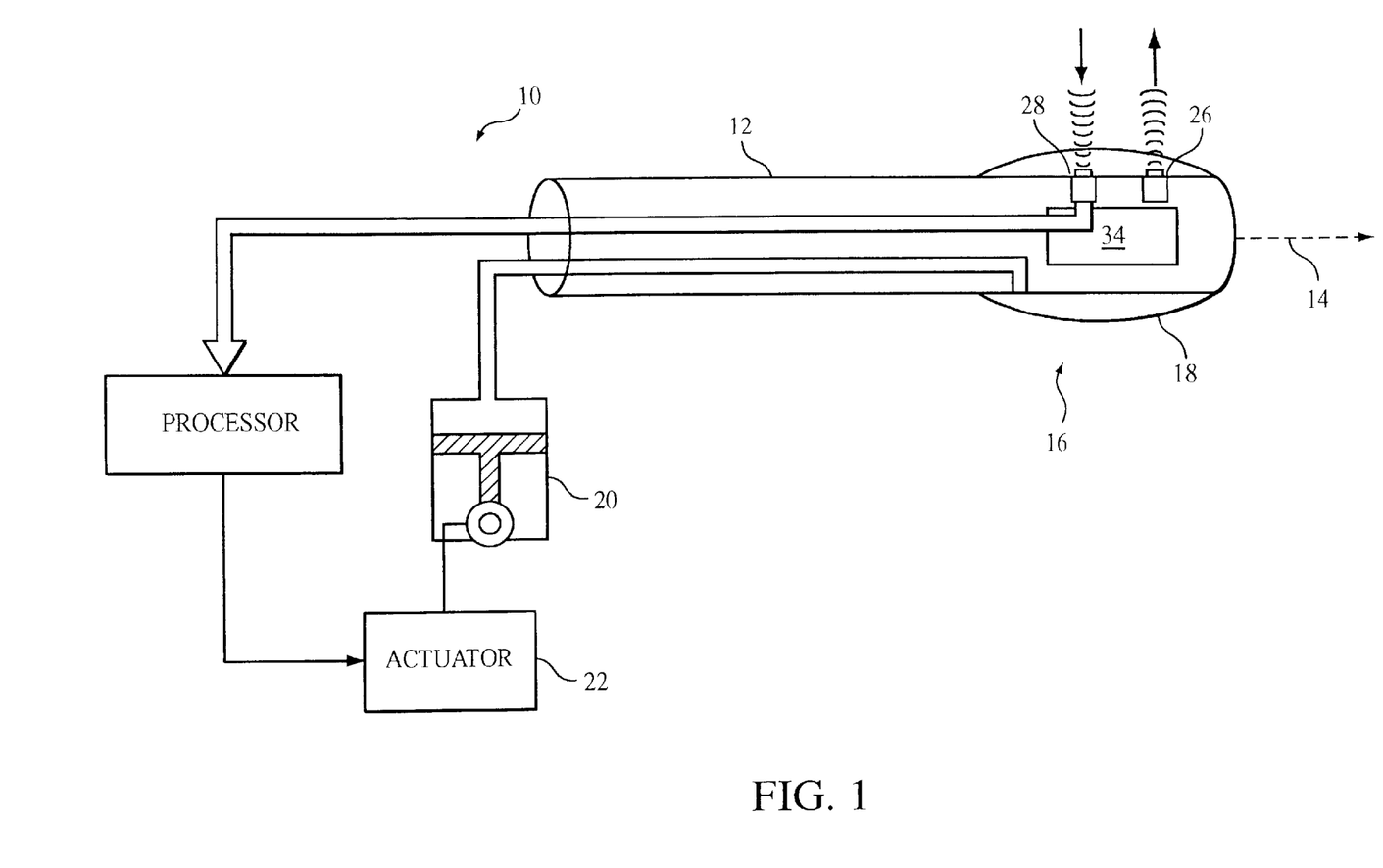
FIG. 1 is a schematic diagram of a balloon catheter with a feedback loop.

Referring now to FIG. 1, an apparatus 10 according to the invention provides a catheter 12 extending along a longitudinal axis 14 and having a distal end 16. A balloon 18 of variable diameter encloses the distal end 16 of the catheter 12. The apparatus shown in FIG. 1 includes a single balloon. However, as will be seen in the discussion of FIG. 5, the principles of the invention are equally applicable to catheters that are surrounded by two or more balloons.

The diameter of the balloon 18 is controlled by varying the amount of a control fluid within the balloon 18. The control fluid can be a gas, such as air, or a liquid, such as saline. What is important is that the control fluid be one that is relatively transparent to infrared radiation at frequencies used in measurements made with the apparatus 10.

The balloon 18 is in communication with a control-fluid source 20 and an actuator 22 whose function is to add or subtract the control fluid from the inside of the balloon 18 through a tube 23 extending between the control-fluid source 20 and the balloon 18. A controller 24 in communication with the actuator 22 causes the actuator 22 to vary the amount of control fluid within the balloon 18 to minimize the difference between a measured diameter of the balloon 18 and a desired diameter of the balloon 18.

Mounted on, or within, the distal end 16 of the catheter 12 is an infrared emitter 26 and an infrared detector 28. The infrared emitter 26 and the infrared detector 28 are coupled to a processor 30 by one or more fiber-optic waveguides 32 extending along the longitudinal axis 14 of the catheter 12.

As used herein, "fiber-optic waveguide" refers to optical fibers that are typically made of glass or a material having a higher dielectric constant than the surrounding medium. The dielectric constant can be constant across the diameter of the fiber or it can follow a particular profile across the diameter of the fiber. In addition, "fiber-optic waveguide" also includes hollow, air-filled tubes with reflecting inner walls, and hollow tubes surrounded by a honeycomb structure of other hollow tubes. Whether wave propagation in the fiber is single-mode or multimode is immaterial to the practice of the invention. Hence, the term "fiber-optic waveguide" is also intended to include single-mode or multi-mode fibers. In addition, the polarization of the wave propagating on the fiber is immaterial to the practice of the invention. Hence, the term "fiber-optic waveguide" includes within its scope waveguides that display birefringence or other properties that are associated with polarization of waves propagating in the waveguide.

Although the embodiment taught herein provides for the use of fiber-optic waveguides to provide communication between the distal end of the catheter and equipment at the proximal end of the catheter, the invention includes other avenues of communication. For example, the distal end of the catheter can include a wireless transmitter for sending data collected at the distal end of the catheter to equipment outside the patient.

Also mounted on or within the distal end 16 of the catheter 12 is an optical subsystem 34 that includes lenses, mirrors, prisms or any combination thereof. The optical subsystem 34 directs or focuses infrared radiation radially across the balloon 18 or longitudinally along the fiber-optic waveguides 32. In one embodiment, the optical subsystem 34 is configured to rotate about the longitudinal axis 14 or translate along the longitudinal axis 14. This enables scanning of various regions of the vessel wall.

Although the particular embodiment described herein includes an infrared emitter 26 and an infrared detector 28, the principles of the invention are applicable to other ranges of electromagnetic radiation such as, but not limited to optical radiation (i.e. radiation that is directly visible to the human eye), or ultraviolet radiation. The invention may also find use in the localized application of ionizing radiation, e.g. X-rays and gamma rays, for eradication of tumors or other undesirable structures. In addition, the principles of the invention are applicable to electromagnetic radiation having wavelengths longer than infrared radiation. Such radiation is commonly referred to as microwave radiation, UHF, VHF, HF, MF, and LF. That the use of one or more of the foregoing frequency bands in medical applications may be limited does not exclude, from the scope of the invention, an apparatus that uses those frequency bands. There may, for example, be non-medical applications for an apparatus 10 that incorporates the principles of the invention. For example, it may be desirable, in a refinery or other chemical processing plant, to monitor conditions in a pipe carrying a fluid, or to apply localized heating (e.g. by microwave radiation) to selected locations along a pipe.

In addition, the principles of the invention are applicable to any emitter or receiver of waves generally. Such waves include mechanical waves, such as acoustic waves in the ultrasonic range, in the megasonic range, or in any other frequency range.

The particular embodiment described herein includes detectors and emitters of generally incoherent radiation. However, the invention is not to be construed as being limited to only incoherent radiation. In particular, the emitter 26 can be a laser or maser, or any source of coherent radiation at any frequency.

The emitter 26 and detector 28 of the invention need not operate at the same frequency. For example, there may be applications in which a transmitted frequency interacts with the coupling medium to stimulate emission, or to cause fluorescence, at a second frequency. In such applications, the detector 28 can be selected to operate at the second frequency.

The emitter 26 and detector 28 of the invention need not operate at a fixed frequency. For example, the response measured by the detector 28 can be integrated over a broad, or narrow, range of detected frequencies. The range of detected frequencies can be contiguous or discrete. Conversely, the emitter 26 can, in some applications, emit radiation over a range of transmitted frequencies and the detector 28 can detect radiation at a single frequency. In such a case, the range of transmitted frequencies can be contiguous or discrete. In other cases, the emitter 26 can transmit radiation over a range of transmitted frequencies and the detector 28 can detect radiation over a range of detected frequencies. Both the range of transmitted frequencies and the range of detected frequencies can be contiguous of discrete. The range of transmitted frequencies can, but need not, overlap with a portion of the range of detected frequencies. However, in some applications, the range of detected frequencies can be identical, or substantially identical to the range of transmitted frequencies.

More generally, the emitter 26 and detector 28 are not restricted to the emission and detection of purely monochromatic waveforms. For example, in some applications it may be of interest to detect an impulse response of a coupling medium. In such a case, the emitter 26 may emit a pulse of radiation at a particular wavelength. The spectrum of such a pulse would include frequency components other than the frequency associated with that wavelength. The detector 28 can then be configured to detect the impulse response. Such an impulse response would also include frequency components other than the frequency associated with that wavelength.

Figure 2:
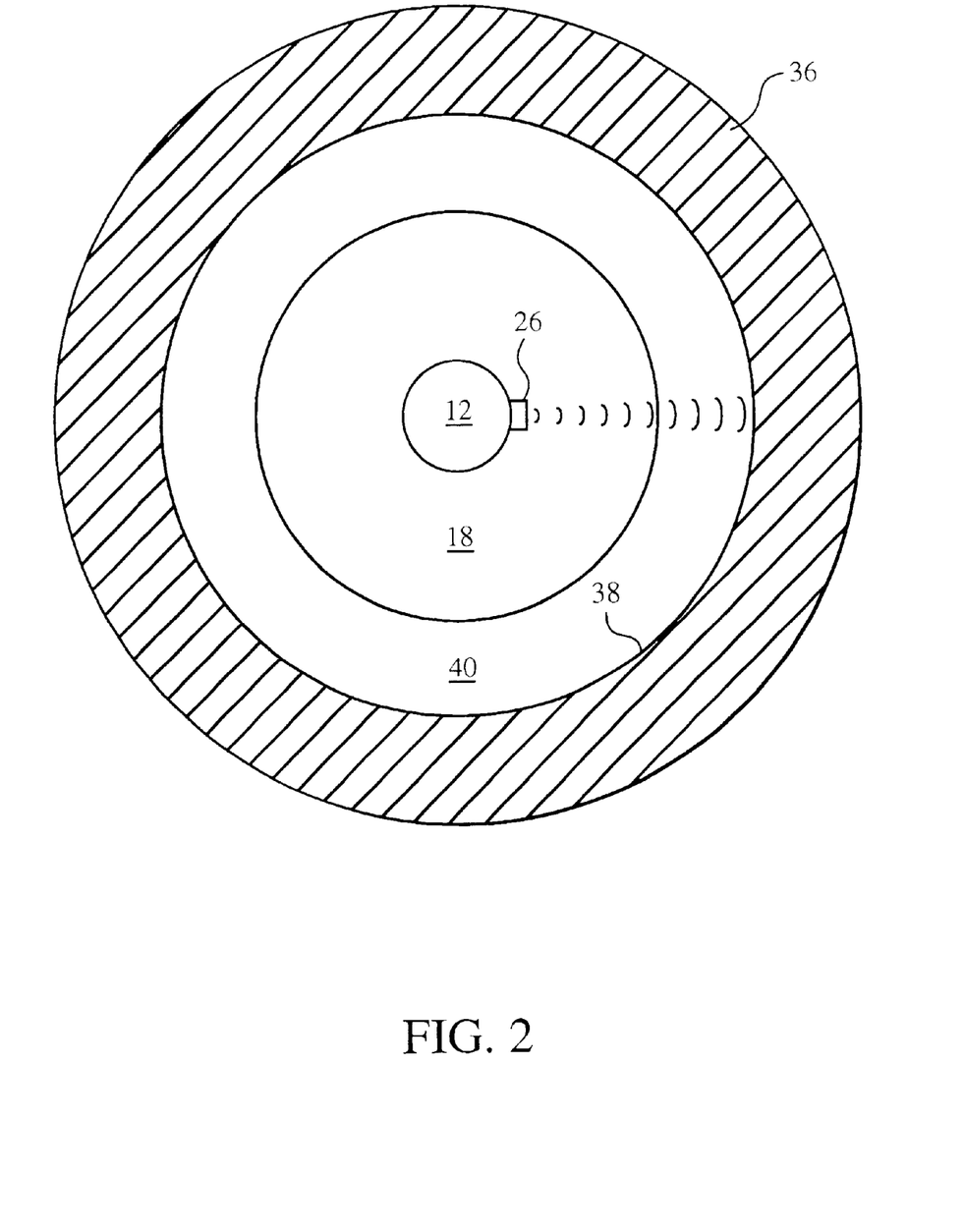
FIG. 2 is a schematic cross-section of the distal end of the catheter deployed in a blood vessel.

FIG. 2 shows a cross-section of the distal end of the catheter 12 deployed within a blood vessel 36. In FIG. 2, the balloon 18 is inflated so as to displace most of the blood that would otherwise flow between the catheter 12 and an inner wall 38 of the blood vessel 36. Surrounding the balloon 18 is an annular gap 40 between the outer wall of the balloon 18 and the inner wall 38 of the blood vessel 36. It is desirable to reduce the extent of this gap 40 as much as possible but without obstructing the flow of blood to tissue downstream from the balloon 18.

The optimal diameter of the inflated balloon 18 depends on the diameter of the blood vessel 36 being imaged or treated. If the balloon diameter is too small relative to the diameter of the blood vessel 36, radiation must cross a larger annulus of blood as it propagates between the catheter 12 and the vessel wall. However, if the balloon diameter is too large, blood flow to tissue downstream from the balloon 18 will be partially or completely interrupted. If the balloon diameter is so large that the balloon 18 makes contact the vessel wall, the force exerted by the balloon 18 on the vessel wall may cause injury to the vessel wall or trigger the rupture of a high-risk plaque hidden behind the vessel wall. A desirable gap 40 between the outer wall of the balloon 18 and the inner wall 38 of the blood vessel 36 is on the order of 100 micrometers. This would include gaps in the range of, for example 50 to 150 micrometers or 75 to 125 micrometers, This might also include gaps in a range such as 90 to 100 micrometers. However, larger gaps, such as gaps in excess of 150 micrometers, or smaller gaps can also be used depending on the specific operating conditions, the wavelength of radiation used, and environmental constraints.

In many cases, the diameter of a blood vessel 36 varies both as a function of position and as a function of time. As a result, the diameter of the balloon 18 must be continuously adjusted to accommodate variations in the diameter of the blood vessel 36. The apparatus 10 thus provides a feedback loop in which a measured value of the gap 40 between the balloon outer wall and the inner wall 38 of the vessel is compared with a desired value of that gap 40. The result of this comparison is used to drive the actuator 22 coupled to the controller 24. If the comparison indicates that the balloon diameter is too small, the actuator 22 causes additional control fluid to enter the balloon 18, thereby increasing the balloon diameter. Conversely, of the comparison indicates that the balloon diameter is too large, the actuator 22 causes withdrawal of control fluid from the balloon 18, thereby reducing the balloon diameter. The extent to which control fluid is added to or removed from the balloon 18 depends on the extent of the difference between the measured extent of the gap 40 and the desired extent of the gap 40.

In the illustrated feedback loop, the infrared detector 28 detects infrared radiation containing information indicative of propagation effects encountered by the first infrared radiation. These propagation effects include scattering and absorption by blood that fills the annular gap 40 between the inner wall 38 of the vessel and the balloon 18, as well as scattering and absorption by the inner wall 38 of the blood vessel 36. Additional propagation effects include Doppler frequency shifts caused by the velocity of blood flowing through the annular gap 40.

In a first embodiment, the processor 30 exploits the fact that blood flowing through the annular gap 40 flows at a higher velocity than blood flowing through an unobstructed portion of the lumen. The difference between the velocity of blood flow in the annular gap 40 and the velocity of the blood flowing through the unobstructed portion of the lumen is thus indicative of the extent of the gap 40. Since the flow of blood varies in response to the heart beat, the effect of the heart beat must first be removed. This can be achieved by providing a second infrared detector and emitter pair located far enough away from the balloon 18 to measure ambient flow velocity in the blood vessel 36. The required distance between the first and second pairs of infrared detectors and emitters depends on the distance required for turbulence caused by the presence of the balloon to dissipate. Preferably, the second infrared emitter and detector pair is placed in a region of laminar flow.

In a second embodiment, the processor 30 exploits the fact that the extent to which infrared radiation is scattered or absorbed by the blood in the gap 40 depends in part on the extent of the gap 40. For example, it is possible to derive a curve, either experimentally or by solving the wave equation with appropriate boundary conditions, that shows, for a particular wavelength, the absorption due to a hemoglobin as a function of distance traversed through a medium containing a known concentration of hemoglobin. The difference in amplitude between the infrared radiation provided by the emitter 26 and the infrared radiation received by the detector 28 can then be used, in conjunction with this curve, to estimate the path length through blood containing the known concentration of hemoglobin.

A difficulty with the direct application of this approach is that the concentration of hemoglobin varies between individuals. Although this concentration can be measured for a particular individual, the resulting variance in the optical properties of the blood must be accounted for to take an accurate measurement.

In addition, the amplitude of the received infrared radiation depends on many other factors. For example, other constituents of the blood may also absorb infrared radiation. Particulate matter in the blood contributes to scattering. As a result of scattering, not all photons traverse the same path through the blood. To the extent that significant numbers of photons traverse a path other than a direct path between the catheter 12 and the inner wall 38 of the blood vessel 36, the processor 30 may consistently underestimate the diameter of the balloon 18.

A single measurement thus embodies propagation effects due to several unknown quantities. In algebraic terms, a single measurement provides one independent equation in several unknowns. To solve for each of the several unknowns, it is necessary to provide as many independent equations as there are unknowns. These additional independent equations are provided by additional measurements made at different wavelengths. The number of independent equations required depends on the number of propagation effects that are to be accounted for.

For example, to remove variations resulting from an individual's hematocrit, two measurements at two wavelengths are required. This is because the hematocrit and the desired absorption represent two unknowns. As is well-known in linear algebra, two independent equations are required to solve for two unknowns. These two independent equations are provided by two measurements at different wavelengths.

To remove variations resulting from both the hematocrit and from scattering, three measurements at three different wavelengths are required. This is because the desired absorption, the hematocrit, and the scattering effects represent three unknowns. As is well-known in linear algebra, a unique solution for three unknowns requires three independent equations. These three independent equations are provided by three measurements at three different wavelengths.

The wavelengths at which measurements are taken are preferably close together. This avoids introducing additional errors due to wavelength dependent variations in propagation effects. For example, if the second measurement were taken at a wavelength that was very different from the wavelength at which the first measurement is taken, then the particles that scattered photons of the first wavelength would no longer scatter photons of the second wavelength. Any estimate of scattering effects calculated by simultaneous solutions of these equations would therefore be meaningless.

In addition, the wavelengths at which measurements are taken are selected such that each of the individual propagation effects can dominate one equation. This ensures that the resulting system of equations defines as nearly orthogonal a basis as possible. As is well-known in linear algebra, such a basis is desirable because the resulting system of equations can then be solved without numerical difficulties resulting from, for example, ill-conditioned matrices.

In one embodiment, a first wavelength is selected so that the absorption due to hemoglobin concentration at that wavelength is much greater than the absorption due to saline. A second wavelength can be selected so that the absorption due to hemoglobin and saline are substantially equal. Suitable values for the first wavelength are between 800 and 900 nanometers. Suitable values for the second wavelength are in the neighborhood of 1100 nanometers.

Figure 3:
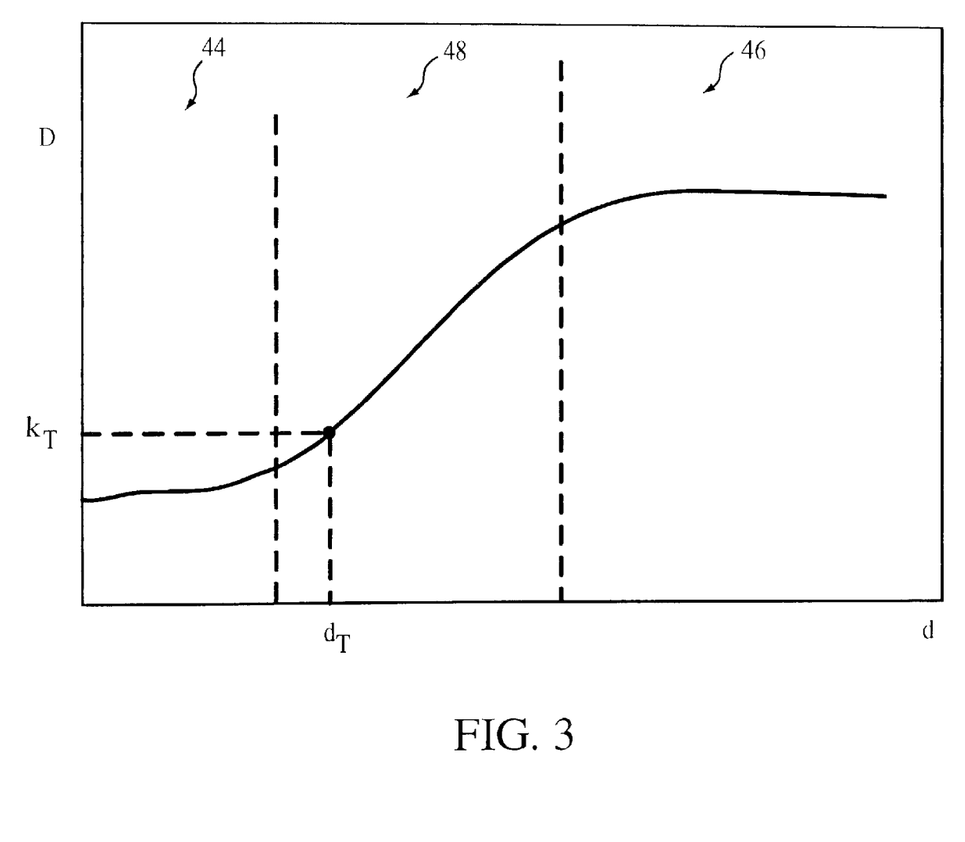
FIG. 3 is a graph of a measured value as a function of the extent of the gap between the vessel wall and the balloon wall.
Figure 4:
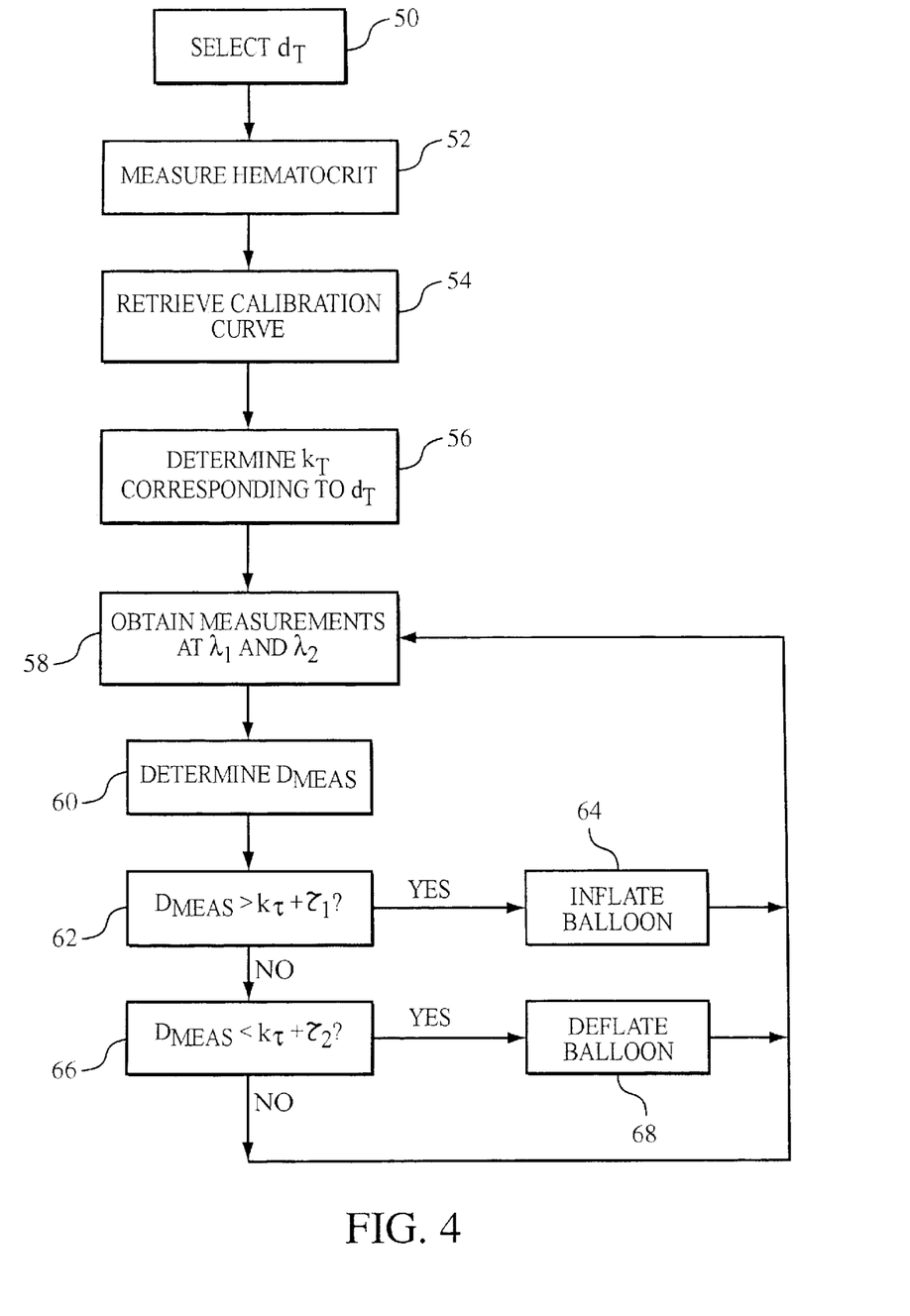
FIG. 4 is a flow-chart showing the algorithm for estimating the extent of the gap between the balloon and the wall of the blood vessel.

FIGS. 3 and 4 illustrate a representative procedure through which two measurements made at different wavelengths are used in a feedback loop to control the extent of the gap 40 between the balloon wall and the vessel wall. The first and second measurement wavelengths $\lambda_1$ and $\lambda_2$ are selected such that the scattering coefficient associated with the first wavelength is greater than the scattering coefficient associated with the second wavelength, the absorption coefficient associated with the first and second wavelengths are approximately equal, and the coefficient of anisotropy associated with the first and second wavelengths are approximately equal. In addition, the blood absorption coefficient for both wavelengths is greater than the vessel wall absorption coefficient for both wavelengths.

For each wavelength $\lambda$, a quantity $A(\lambda)$ is defined as:

$$A(\lambda) = -\ln\left(\frac{R(\lambda)}{R_o(\lambda)}\right)$$

where $R(\lambda)$ is the reflectance associated with wavelength $\lambda$ and $R_o(\lambda)$ is the reflectance that would be measured if 100% of the power transmitted into the coupling medium were reflected. The quantity $A(\lambda)$ is measured for each of the two measurement wavelengths $\lambda_1$ and $\lambda_2$. This results in the measured ratio D defined as:

$$D = \frac{A(\lambda_1)}{A(\lambda_2)}$$

Note that D can also be defined in terms of any ratio of a function of $A(\lambda_1)$, a corresponding function of $A(\lambda_2)$, or a function of $A(\lambda_1)$ and $A(\lambda_2)$.

FIG. 3 shows, for a particular hematocrit, a calibration curve 42 of the measured ratio D as a function of the extent of the gap d between the balloon wall and the wall of the blood vessel. A calibration curve 42 such as that shown in FIG. 3 can be obtained in advance through experimental measurements, through Monte Carlo simulation, or through modeling the wave propagation by diffusion theory. A typical calibration curve 42 can be divided into three portions: a first, relatively flat portion 44 in which radiation at both wavelengths interacts primarily with the vessel wall, a second, relatively flat portion 46, in which radiation at both wavelengths interacts primarily with the blood in the gap 40, and a third portion 48, in which radiation at both wavelengths interacts with both the blood in the gap 40 and with the vessel wall. Thus, if the hematocrit is known, a measured ratio D can be mapped to a gap d by referring to a calibration curve 42 of the type shown in FIG. 3. In most cases, the desired extent $d_t$ will be in the third region 48.

FIG. 4 shows a representative procedure for controlling the diameter of the balloon when two independent measurements at two different wavelengths are available. First, a desired extent of the gap $d_t$ is selected 50. Then, the hematocrit is measured 52. This measurement can be performed in advance through laboratory analysis. Alternatively, a hematocrit estimate can be made by a separate absorption measurement. A calibration curve of the type shown in FIG. 3 is retrieved 54 from a calibration database. Using that curve, a value $k_t$ corresponding to the desired extent $d_t$ is obtained 56.

Measurements are then obtained 58 at the two wavelengths $\lambda_1$ and $\lambda_2$ and used to evaluate 60 a measured value of D, namely $D_{meas}$. The value of $k_t$ is then compared with $D_{meas}$. If $D_{meas}$ exceeds $k_t$ by more than a first pre-selected threshold $\tau_1$ 62, the balloon is inflated 64, either by a calculated amount or incrementally. If $k_t$ exceeds $D_{meas}$ by more than a second pre-selected threshold $\tau_2$ 66, the balloon is deflated 68, either by a calculated amount or incrementally. If neither of these conditions is true, then the gap has an extent that is within a pre-defined tolerance of the correct value.

Regardless of the outcome of the comparison of $D_{meas}$ and $k_t$, subsequent measurements at $\lambda_1$ and $\lambda_2$ are obtained. This enables the feedback control system to continuously monitor the extent of the gap and to dynamically adjust that extent as the distal tip 16 of the catheter 12 is moved to vessels or portions of a vessel having different inner diameters.

Figure 5:
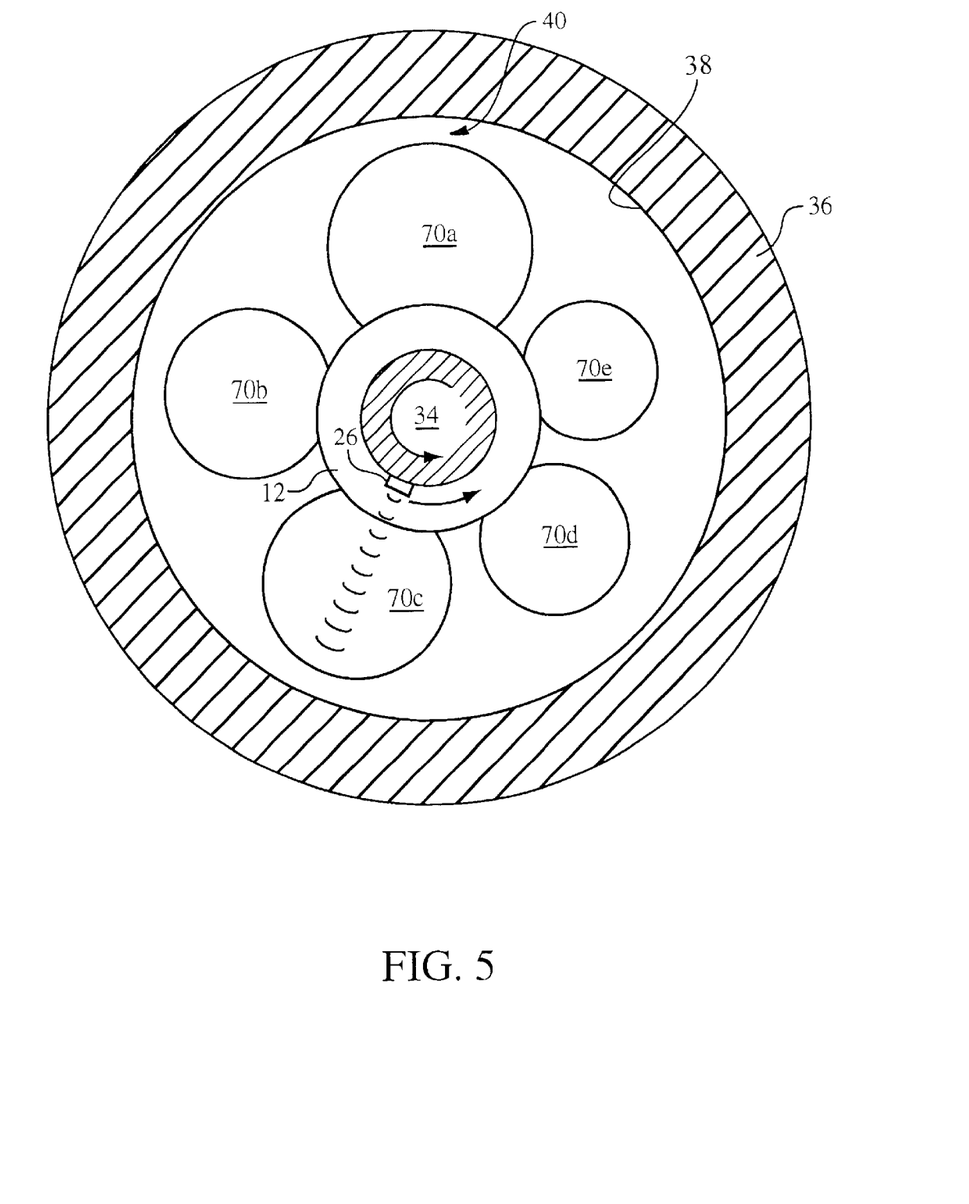
FIG. 5 is a schematic, cross-sectional view of a multiple-balloon catheter within a blood vessel.

In another embodiment, shown in cross-section in FIG. 5, a plurality of balloons 70a–e is circumferentially disposed around the catheter 12. In this embodiment, the optical subsystem 34 is a rotating optical subsystem 34 that directs an infrared beam to each of a plurality of circumferentially spaced locations on the inner wall 38. Each such measurement provides information on the distance between a portion of the inner wall 38 of the blood vessel 36 and an outer wall of that balloon that is adjacent to that portion of the inner wall 38. Each of the plurality of balloons is individually controllable by the actuator 22. Thus, the extent of the gap 40 (which in this case is no longer an annular gap as in FIG. 2) between the outer wall of the balloon 70a–e and the inner wall 38 of the blood vessel 36 can be maintained at a selected value even if the cross-sectional shape of the blood vessel 36 deviates significantly from being circular.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for controlling an extent of a gap between a wall of a balloon catheter and a wall of a lumen, the gap being filled with a coupling fluid, the method comprising:
   transmitting first radiation through the coupling fluid;
   receiving second radiation, the second radiation containing information indicative of propagation effects encountered by the first radiation;
   determining, on the basis of the second radiation, a measured extent of the gap; and
   controlling inflation of the balloon catheter to minimize a difference between the measured extent of the gap and a desired extent of the gap.

2. The method of claim 1, wherein transmitting first radiation comprises transmitting radiation at a first wavelength at which propagation effects in the coupling fluid are dominated by a first constituent of the coupling fluid.

3. The method of claim 2, wherein transmitting first radiation further comprises transmitting radiation at a second wavelength at which propagation effects in the coupling fluid are dominated by a second constituent of the coupling fluid.

4. The method of claim 3, wherein transmitting first radiation further comprises transmitting radiation at a third wavelength at which propagation effects in the coupling fluid are dominated by neither the first constituent nor the second constituent.

5. The method of claim 4, further comprising:
   selecting the first constituent to be hemoglobin, and
   selecting the second constituent to be saline.

6. The method of claim 1, wherein transmitting the first radiation comprises:
   selecting a plurality of wavelengths; and
   transmitting radiation at each of the plurality of wavelengths.

7. The method of claim 1, wherein receiving second radiation comprises receiving attenuated radiation at the first wavelength, the extent of the attenuation being indicative of the extent of the gap.

8. The method of claim 1, wherein receiving second radiation comprises receiving radiation at a second wavelength, the difference between the first and second wavelengths being indicative of velocity of the coupling fluid, the velocity of the coupling fluid being indicative of the extent of the gap.

9. The method of claim 1, wherein determining the measured extent of the gap comprises removing scattering and absorption effects resulting from propagation of the first radiation through the coupling fluid.

10. The method of claim 1, wherein determining the measured extent of the gap comprises removing effects from pulsatile flow of the coupling fluid.

11. The method of claim 1, wherein controlling inflation of the balloon catheter comprises:
    delivering control fluid to the catheter balloon when the desired extent of the gap exceeds the measured extent of the gap; and
    withdrawing control fluid from the catheter balloon when the measured extent of the gap exceeds the desired extent of the gap.

12. The method of claim 1, wherein controlling inflation of the balloon catheter comprises:
    changing a quantity of control fluid in the catheter balloon by incremental amounts until the difference between the measured extent of the gap and the desired extent of the gap is within a pre-selected range.

13. The method of claim 1, wherein controlling inflation of the balloon catheter comprises:
    changing the quantity of control fluid in the catheter balloon by an amount that depends on the difference between the measured extent of the gap and the desired extent of the gap.

14. The method of claim 1, wherein transmitting radiation through the coupling fluid comprises:
    defining a plurality of radial directions, each of the radial directions extending radially outward from a longitudinal axis of the catheter; and
    transmitting a corresponding plurality of radiation beams in each of the radial directions.

15. The method of claim 14, wherein controlling inflation of the balloon catheter comprises controlling inflation of each of a plurality of balloons circumferentially disposed around the longitudinal axis of the catheter, each of the plurality of balloons being inflated to an extent required to achieve a pre-selected gap between the balloon and the wall of the lumen.

16. The method of claim 1, wherein transmitting first radiation comprises transmitting infrared radiation.

17. The method of claim 1, wherein receiving second radiation comprises receiving infrared radiation.

18. A method for controlling an extent of a gap between a wall of a balloon mounted on a catheter and a wall of a lumen into which the catheter is inserted, the method comprising:
    obtaining a feedback signal having information indicative of whether the extent of the gap is greater than or less than a desired value;
    in response to the feedback signal, controlling a size of the balloon to cause the extent of the gap to approach the desired value.

19. An apparatus comprising:
    a catheter for insertion into a lumen;
    a balloon disposed on the catheter, the balloon defining a gap between a wall of the lumen and a wall of the balloon;
    a radiation source disposed within the balloon for transmitting radiation through the balloon wall and into coupling fluid present in the gap; and
    a feedback loop including
        a radiation detector disposed within the balloon to receive radiation from the coupling fluid through the balloon wall,
        a processor in communication with the radiation detector for determining, on the basis of a signal provided by the radiation detector, a measured extent of the gap, and
        a controller in communication with the processor for controlling inflation of the balloon to achieve a desired extent of the gap in response to the measured extent of the gap.

20. The apparatus of claim 19, wherein the radiation source comprises an infrared emitter.

21. The apparatus of claim 19, wherein the radiation detector comprises an infrared detector.

22. The apparatus of claim 19, further comprising control fluid to be delivered to the balloon to change the extent of the gap.

23. The apparatus of claim 19, wherein the processor is configured to determine the extent of the gap on the basis of absorption of radiation transmitted by the radiation source, the extent of the absorption being indicative of the extent of the gap.

24. The apparatus of claim 19, wherein the processor is configured to determine the extent of the gap on the basis of velocity of coupling fluid in the gap, the velocity of the coupling fluid being indicative of the extent of the gap.

25. The apparatus of claim 19, further comprising a calibration database in communication with the processor.

26. The apparatus of claim 19, wherein the controller is configured to control inflation of the balloon by changing a quantity of control fluid in the balloon by incremental amounts until the difference between the measured extent of the gap and the desired extent of the gap is within a pre-selected range.

27. The apparatus of claim 19, wherein the controller is configured to control inflation of the balloon by an amount that depends on the difference between the measured extent of the gap and the desired extent of the gap.

28. The apparatus of claim 19, further comprising a plurality of balloons circumferentially disposed around the distal end of the catheter, each of the balloons having a size that is controllable by the controller.

29. The apparatus of claim 28, wherein the controller is configured to select a balloon from the plurality of balloons and to change the size of the balloon to control an extent of a gap between the selected balloon and the wall of the lumen.

30. An apparatus for controlling an extent of a gap between a wall of a balloon mounted on a catheter and a wall of a lumen into which the catheter is inserted, the apparatus comprising:
- a radiation detector mounted within the balloon for generating a feedback signal having information indicative of whether the extent of the gap is greater than or less than a desired value;
- a feedback loop for receiving the feedback signal and controlling a size of the balloon to cause the extent of the gap to approach the desired value.

* * * * *